United States Patent
Stanislav et al.

(10) Patent No.: US 10,381,193 B2
(45) Date of Patent: Aug. 13, 2019

(54) SCANNING TRANSMISSION ELECTRON MICROSCOPE WITH AN OBJECTIVE ELECTROMAGNETIC LENS AND A METHOD OF USE THEREOF

(71) Applicants: TESCAN Brno s.r.o., Brno (CZ); TESCAN TEMPE, LLC., Tempe, AZ (US)

(72) Inventors: Petras Stanislav, Predni Ptakovice (CZ); Lencova Bohumila, Kurim (CZ); Benner Gerd Ludwig, Aalen (DE)

(73) Assignees: TESCAN BRNO, S.R.O., Brno (CZ); TESCAN TEMPE, LLC, Tempe, AZ (US)

( * ) Notice: Subject to any disclaimer, the term of this patent is extended or adjusted under 35 U.S.C. 154(b) by 0 days.

(21) Appl. No.: 15/926,501

(22) Filed: Mar. 20, 2018

(65) Prior Publication Data
US 2018/0269030 A1    Sep. 20, 2018

(30) Foreign Application Priority Data
Mar. 20, 2017  (EP) .................... 17000453

(51) Int. Cl.
| | | |
|---|---|---|
| H01J 37/26 | (2006.01) | |
| H01J 37/141 | (2006.01) | |
| H01J 37/244 | (2006.01) | |
| G01N 23/2251 | (2018.01) | |
| G01N 23/20058 | (2018.01) | |
| H01J 37/28 | (2006.01) | |

(52) U.S. Cl.
CPC ...... *H01J 37/268* (2013.01); *G01N 23/20058* (2013.01); *G01N 23/2251* (2013.01); *H01J 37/1413* (2013.01); *H01J 37/244* (2013.01); *H01J 37/28* (2013.01); *H01J 2237/0492* (2013.01); *H01J 2237/141* (2013.01); *H01J 2237/2802* (2013.01)

(58) Field of Classification Search
USPC ...................................................... 250/311
See application file for complete search history.

(56) References Cited

U.S. PATENT DOCUMENTS

6,531,697 B1 * 3/2003 Nakamura .......... H01J 37/1471
                                                          250/302
7,105,816 B2    9/2006 Kamiya et al.
(Continued)

*Primary Examiner* — Kiet T Nguyen
(74) *Attorney, Agent, or Firm* — Thedford I Hitaffer; Hitaffer & Hitaffer, PLLC (57) ABSTRACT

The object of the present invention provides a scanning transmission electron microscope with the ability to formed at least one diffraction pattern. The scanning electron microscope comprises an electron source, which is configured to provide primary electron beam, a condenser lens system, an objective electromagnetic system, a projection lens system and a detection system, in addition, the objective electromagnetic lens consists of an upper pole piece and a lower pole piece, wherein each pole piece comprises a pole piece face, which is a flat surface oriented towards a sample plane. A salient feature of the present invention is to form at least one diffraction pattern located in the distance from the lower pole piece face outside the pole piece gap, wherein the pole piece gap is the space between the upper pole piece face and the lower pole piece face.

16 Claims, 6 Drawing Sheets

(56) References Cited

U.S. PATENT DOCUMENTS

| | | |
|---|---|---|
| 8,080,791 B2 | 12/2011 | von Harrach et al. |
| 8,476,589 B2 | 7/2013 | Benner et al. |
| 9,543,115 B2 | 1/2017 | Benner et al. |
| 2013/0256558 A1* | 10/2013 | Dietl ...................... H01J 37/26 |
| | | 250/440.11 |

* cited by examiner

SCANNING TRANSMISSION ELECTRON MICROSCOPE WITH AN OBJECTIVE ELECTROMAGNETIC LENS AND A METHOD OF USE THEREOF

CROSS-REFERENCE TO RELATED APPLICATION

This application is claims priority from European Patent Application No. 17000453.5, filed Mar. 20, 2017, the disclosure of which is incorporated herein by reference.

FIELD OF THE INVENTION

The present invention relates to a scanning transmission electron microscope.

STATE OF THE ART

A scanning transmission electron microscope (STEM) is a powerful instrument for an analysis of the morphology, structure and composition of various samples. In the basic arrangement, STEMS typically comprise a source of electrons, a condenser lens system, an objective lens, a projection lens system and a detection system.

The electron beam generated in the electron source passes through the condenser lens system which typically consists of three lenses (C1, C2 and C3). Moreover, an aperture used for the restriction of the electron beam is placed either above or below the condenser system. In addition to this condenser aperture, the set of condenser lenses is used for changing parameters of the electron beam.

After adjustment of the parameters, the electron beam impinges on a sample which is normally placed symmetrically in the centre of the pole piece gap of the objective electromagnetic lens. The transmitted electrons carry information about the sample down to the atomic scale. The electrons which pass through the sample with no scattering or with a small scattering angle are called bright field (BF) electrons. All scattered electrons lying outside the primary illumination cone are called dark field (DF) electrons.

Besides BF/DF electrons, Xray radiation resulting from the interaction of the primary beam of electrons with the atoms of the sample can be collected and analysed to determine the elemental composition of the sample.

Essential parts of the STEM are scanning coils which are used for scanning a fine beam spot over a field of view on the sample. The scanning coils are placed above the objective electromagnetic lens (or more specifically above the upper pole piece) shift the spot, which has a convergence angle in the range of 10 mrad, over the sample.

From the point of view of particle optics, the objective electromagnetic lens consists of at least two lenses. The field above the sample forms the so-called pre-field lens and the field below the sample generates one (or more) imaging lenses. Here and afterwards, the expression 'above' the sample means the space between the electron source and the sample (or sample plane) whereas the expression 'below' the sample corresponds to the situation where something is located between the sample plane and the detector.

The electron gun—consisting of a cold or heated electron emitter, an extraction or control electrode and (multiple) accelerator electrodes—generates a real or virtual electron source (cross-over). This cross-over is focused by the condenser lens system and the objective pre-field lens at the sample. The transmitted electrons are focused by the objective imaging lens(es) according to their scattering angle in a diffraction pattern (BF/DF) located in the back focal plane of the objective lens. This diffraction pattern is then magnified by the projection lens system on the recording system (CMOS camera, STEM detector).

Although the SEM instruments are at the top of the technological branch, imperfections can still be found in the form of lens aberration, such as spherical aberration. To minimize the axial aberration, a pole piece gap can be reduced till the saturation level of the objective electromagnetic lens is reached. However, there are limitations in the reduction of the pole piece gap for the STEMs operating at up to 100 kV not only because of the mechanical stand point but also because there has to be a balance between minimum resolution and maximum sample tilt and detection efficiency.

Various technical solutions were used for the detection of transmitted electrons of both BF and DF. In the U.S. Pat. No. 7,105,816, a specialized STEM with high angle annular dark field detector arranged under the objective electromagnetic lens is claimed, in which the detection range of the high angle scattered electrons is changed by mechanical movement of said detector along the optical axis. In addition, the bright field detector which is placed under the high angle annular dark field detector is used for the detection of electrons which pass through the sample without (or with very small) scattering.

In U.S. Pat. No. 9,543,115 B1, an additional lens under the objective electromagnetic lens is used to adjust the range of the scattering angle.

Both of these technical solutions limit the use of de-scanning coils which are necessary for higher scan fields and precession. Furthermore, due to a missing multi-stage projector lens system, the diffraction pattern is out of focus which does not allow the use of some diffraction applications (CBED, SA diffraction).

Besides the BF and DF signals, the other types of information such as x-ray could be gained from the sample. An appropriate detection system for this additional information has to be arranged in the space near the sample.

In the U.S. Pat. No. 8,476,589, a double detector system is described where at least one detector is arranged above the sample plane and at least one detector is placed below the sample plane. In addition to the technical complicacy, the price increase caused by two different detectors also represent negative aspect of this technical solution.

In addition, the solution on FIG. 3 in U.S. Pat. No. 8,080,791 shows two detectors arranged above the sample asymmetrically in the pole piece of the objective lens. The disadvantage of this arrangement is that the pre-field provides much higher aberration coefficients when the sample is arranged close to the lower pole piece. Since the minimization of the aberration coefficients is crucial for the high-resolution performance of the microscope, placing the detectors above the sample on the expense of higher aberrations is not convenient.

SUMMARY OF THE INVENTION

The above mentioned disadvantages are overcome by the present invention of a scanning transmission electron microscope comprising an electron source configured to provide a primary electron beam with cross-over, a condenser system, an objective electromagnetic lens comprising an upper pole piece and a lower pole piece forming a pole piece gap configured to provide a pre-field and a post-field with respect to a sample plane located inside the pole piece gap, wherein the upper pole piece comprises an upper pole piece face and the lower pole piece comprises a lower pole piece face. The scanning transmission electron microscope further comprises a projection lens system comprising at least a first projection lens and a second projection lens, and a detection system. The object of the present invention is to provide the high-resolution performance of said scanning transmission electron microscope at energies below the 100 kV by the operation mode where at least one diffraction pattern is formed in the distance from the lower pole piece face outside the pole piece gap, wherein the distance between lower pole piece face and at least one diffraction pattern is in the interval (0-1) mm.

Another salient feature of the presented scanning transmission electron microscope is that a virtual image plane of the objective electromagnetic lens is located at least 15 mm above the centre of the pole piece gap.

Yet another feature of the presented scanning transmission electron microscope is that the post-specimen field generated by the objective electromagnetic lens is composed of a triple lens, wherein the triple lens is formed below the sample plane. A first lens of the triple lens is configured to generate a cross-over image in the image plane and a first diffraction pattern in the first diffraction plane, wherein the cross-over image plane is formed in the vicinity of the principal plane of the second lens of the triple lens, wherein the first diffraction plane is located between the first and the second lens of the triple lens. Further on, the first diffraction pattern is projected by the second lens of the triple lens into the second diffraction plane, located in the vicinity of the principal plane of the third lens of the triple lens, wherein the second diffraction pattern is transferred with variable magnification by the projection lens system into the detection system.

The above mentioned features are used in way that the scanning transmission electron microscope is able to work in a mode where the sample plane is placed asymmetrically between the upper pole piece face and the lower pole piece face. More specifically, the distance between the sample plane and the upper pole piece face is smaller than the distance between the sample plane and the lower pole piece face.

The asymmetrical arrangement of the sample plane allows to put at least one EDS detector between the sample plane and the lower pole piece face. Such an arrangement is a great advantage in the operation mode where the X-ray radiation caused by the interaction of the electrons of a primary beam with the sample is used. In comparison with the prior art, present arrangement allows to put quite large detector or detectors very close to the sample.

In another embodiment, the scanning transmission electron microscope further comprises at least two EDS detectors, wherein two EDS detectors are arranged opposite to each other. Such an arrangement leads to doubling of the collection efficiency of the X-ray detection.

In yet another embodiment at least, one EDS detector is mounted on an arm, wherein the arm is configured to provide a linear movement of the EDS detector. In addition, the scanning transmission electron microscope further comprises the beam blanker connected to the control unit and at least one EDS detector connected to the same control unit. The principal of the EDS detector is that it is configured to collect the X-ray signal raised by interaction of the primary electron beam with the sample, wherein it is configured to transform X-ray signal to electrical signal. In this mode, the control unit is configured to blank the primary electron beam in the case the EDS intensity of the X-ray radiation exceed EDS a defined threshold value.

In yet another embodiment the scanning transmission electron microscope further comprises an ultra-high angle annular dark field detector, which is placed between the image plane generated by the first lens of the above mentioned triple lens and the lower pole piece face.

The above mentioned operation mode of the scanning transmission electron microscope allows to place an intermediate chamber between the first projection lens and the second projection lens.

The presented invention also provides a method of providing double diffraction pattern, bright field image and dark field image in the scanning transmission electron microscope comprising an electron source configured to provide a primary electron beam with cross-over, a condenser system. The scanning transmission electron microscope further comprises of an objective electromagnetic lens, which comprises an upper pole piece and a lower pole piece configured to provide a pre-field and a post-field, wherein the upper pole piece comprises an upper pole piece face and the lower pole piece comprises a lower pole piece face, a sample plane, a projection lens system and a detection system. It is an object of the present invention that the electrons passing the sample plane generates at least one diffraction pattern, wherein at least one diffraction pattern is located in the distance from the lower pole piece face outside the pole piece gap. More specifically, the distance between lower pole piece face and at least one diffraction pattern is in the interval (0-1) mm. In addition, a virtual cross-over image is generated in a virtual image plane, which located at least 15 mm above the centre of the pole piece gap.

Another salient feature of the method is that the post-field generated by the objective electromagnetic lens acts as a triple lens, where the triple lens is formed below the sample plane. The first lens of the triple lens generates a cross-over image in the image plane and a first diffraction pattern in the first diffraction plane. The image plane is located in the second lens of the triple lens, while the diffraction plane is between the first and the second lens of the triple lens. Subsequently, the first diffraction pattern is projected by the second lens of the triple lens into the second diffraction plane which is located close to the principal plane of the third lens of the triple lens. Finally, the second diffraction pattern is transferred by the projection lens system with variable magnification into the detection system.

In another embodiment, the condenser lens system generates a cross-over image in the entrance object plane of the pre-field lens.

Since it is possible to use another operation mode, the present invention also brings a method of providing a single diffraction pattern, bright field image and dark field image in the scanning transmission electron microscope which comprises an electron source configured to provide a primary beam with cross-over, a condenser system, an objective electromagnetic lens. The objective electromagnetic lens comprises an upper pole piece and a lower pole piece which are configured to provide a pre-field and a post-field with respect to a sample plane located inside the pole piece gap. In addition, the upper pole piece comprises an upper pole piece face and the lower pole piece comprises a lower pole piece face. The scanning transmission electron microscope further comprises a projection lens system and a detection system. It is a salient feature of said method that the post-field generated by the objective electromagnetic lens acts as a single lens, where the single lens is formed between the sample plane and the lower pole piece face. The single lens generates a virtual cross-over image in the virtual image plane and a single diffraction pattern, which is located in the distance from the lower pole piece face outside the pole piece gap. More specifically, the distance between lower pole piece and at least one diffraction pattern is in the interval (0-1) mm. Subsequently, the diffraction pattern is transferred with variable magnification by the projection lens system into the detection system.

In yet another embodiment the third condenser lens C3 generates a focused cross-over image in the sample plane.

DETAILED DESCRIPTION

Figure 1:
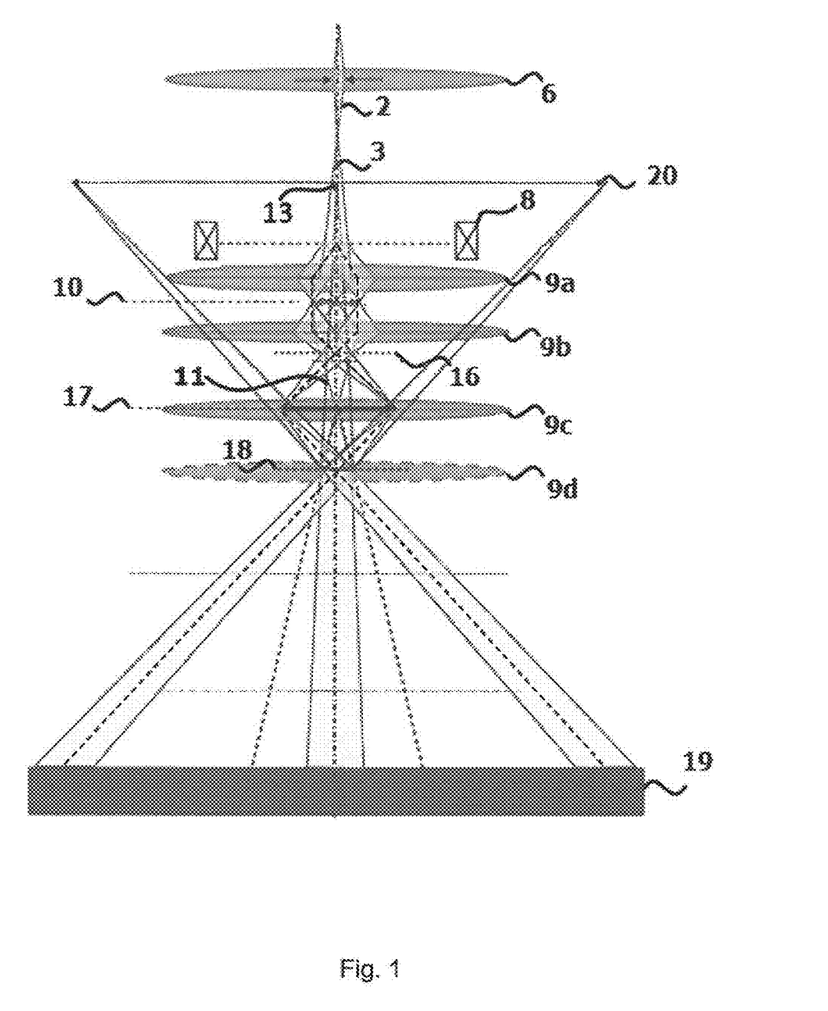
FIG. 1 is a schematic drawing of the objective electromagnetic lens in DDI mode.

FIG. 1 is a schematic drawing of the electron beam inside the objective electromagnetic lens 9. Such an objective electromagnetic lens 9 has generally two pole pieces between which the magnetic field—generated by coils placed inside the iron circuit of the objective electromagnetic lens 9—protrudes into the sample plane 10 which is placed between said pole pieces. The upper pole piece as well as the lower pole piece are expanded parts of the objective electromagnetic lens 9 which have generally faces, i.e. flat surfaces oriented towards the sample plane 10. In addition, the space between the upper pole piece face 26 and the lower pole piece face 27 is named pole piece gap. The magnitude of the magnetic field generated by the coils of objective electromagnetic lens 9 affects the electrons before they enter the sample as well as when they emerge from the sample. This has a crucial effect on the following projection of the scattered electrons.

The primary beam 2 is scanned over the sample by the scanning coils 8 (here schematically portrayed by a single deflection system in the front focal plane of the objective electromagnetic lens 9). The magnetic field of the objective electromagnetic lens 9 is so strong that it has the effect of four different lenses called a pre-field lens 9a, an object lens 9b, a first diffraction lens 9c and a second diffraction lens 9d. Here and afterwards, the terms electromagnetic lens and lens will be used differently. The electromagnetic lens is a physical part of the microscope comprising the coils which produce magnetic flux guided in the magnetic circuit with pole pieces which direct and shape the magnetic field. The lens is the field produced in the gap, usually inside the inner core of the electromagnetic lens, which has, for passing charged particles such as electrons, the effect of converging lens(es) characterized by the focal plane and the principal plane. In summary, the lens is a result of the magnetic field acting on electrons generated by the electromagnetic lens.

Pre-field lens 9a is configured to project the cross-over image of the condenser lens system to the sample plane 10.

In other words, the pre-field generates a fine focused beam spot on the sample located in the sample plane 10. At this point, two different groups of rays need to be distinguished. The first group comprises the axial rays 11 which enter and leave one point of the sample under a defined convergence angle. A fraction of these electrons is scattered in the forward direction when they pass through the sample which means that they change their direction. These electrons as well as the un-scattered electrons are further bent back towards the optical axis 3 by the object lens 9b and are focused according to their origin in the sample in the image plane 17, i.e. they create an image near the principal plane of the diffraction lens 9c. Thus, the un-scattered electrons as well as electrons scattered in the forward direction are not further affected by the diffraction lens 9c. Consequently, the axial rays 11 are slightly bent towards the optical axis 3 by the second diffraction lens 9d in such a way that the back projected axial rays 11 form a virtual image 13 in the virtual image plane 20 above the pre-field lens 9a. The second group of electrons, the so-called field rays 12 (dashed lines), enters the sample perpendicularly to the optical axis 3. After passing the sample, these field rays 12 are focused by the object lens 9b into the back focal plane of this lens. Accordingly, all electrons with the same scattering angle are also focused in this plane but in an off-axis point and they create a first diffraction pattern in the first diffraction plane 16 between the object lens 9b and the image plane 17. The first diffraction pattern is then projected by the first diffraction lens 9c from the first diffraction plane 16 into the second diffraction plane 18 close to the principal plane of the second diffraction lens 9d, meaning that this lens does not affect the field rays 12, and the second diffraction pattern stays close to the lower pole piece face 27. Finally, the second diffraction pattern is projected into the detection system 15 (not shown) by the projection lens system 19.

Since the sample plane 10 position and the excitation of objective electromagnetic lens 9 is set as it was described, the first diffraction pattern as well the second diffraction pattern are located inside the objective electromagnetic lens. More preciously, the first diffraction pattern is located between the sample plane 10 and the lower pole piece face 27, while the second diffraction pattern is formed in the vicinity of the lower pole piece face 27 (in the range of 0-1 mm) but outside the pole piece gap. Simultaneously, the axial rays 11 form the virtual cross-over image 13 in the virtual image plane 20 which is located above the upper pole piece. Such an operation mode could be called Double Diffraction Image (DDI) mode because two diffraction patterns are generated.

In the preferred embodiment, the distance of the virtual image plane 20 from the centre of the pole piece gap is in the range of (15-70) mm. Such an arrangement gives a magnification of the image in the range of (10×-30×).

In another embodiment, the excitation of the objective electromagnetic lens 9 is lower. In that case, the post-field of the objective electromagnetic lens 9 has an effect of only one lens and only one diffraction pattern is formed (for that reason it could be called a Single Diffraction Image (SDI) mode). However, if the condition is met, this single diffraction pattern is generated in the same plane as the second diffraction pattern in the DDI mode. Thus the projection system 19 can be operated in the same mode for both DDI mode and SDI mode (as described below, see FIG. 2). The excitation of the objective electromagnetic lens 9 in the SDI mode is only about one third of that in DDI mode. Consequently, the pre-field lens 9a is too weak in the SDI mode for focusing the beam at the sample. For that reason, the third condenser lens C3 6 has to be used for focusing the beam. Since the radius of the maximum scan field is proportional to the focal length of the pre-field lens 9a, SDI mode allows for higher scan fields.

Since the magnetic field in the DDI mode is strong, the sample plane 10 has to be shifted towards the upper pole piece face 26. In ordinary STEMs, the sample plane 10 is placed in the middle between the upper pole piece face 26 and the lower pole piece face 27. The distance between both pole pieces is about 5 mm. Thus, the sample plane 10 is approximately 2.5 mm from each pole piece face.

In a preferred embodiment, according to this invention, the sample plane 10 is approximately 3 mm from the upper pole piece face 26 and approximately 9 mm from the lower pole piece face 27. In another embodiment, the distance between pole pieces as well as between the sample plane 10 and pole piece faces could be different.

Figure 5:
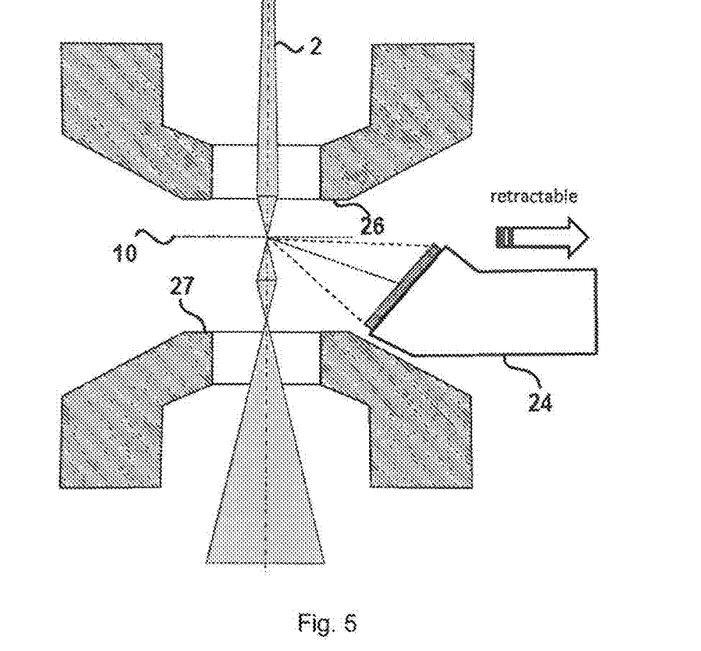
FIG. 5 is a schematic drawing of the arrangement of EDS detector inside the objective electromagnetic lens.
Figure 6:
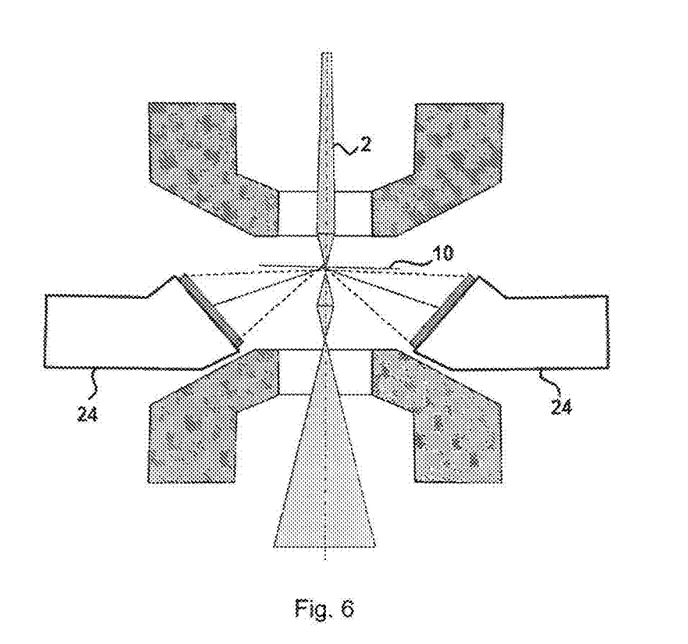
FIG. 6 is a schematic drawing of the arrangement of two EDS detectors inside the objective electromagnetic lens.

The asymmetrical arrangement of the sample offers the opportunity to place an Energy Dispersive X-ray (EDS) detector 24 with a large sensitive detection area very close below the sample. Such an arrangement has several advantages. One of them is increased detection efficiency. Furthermore, a doubling of the detection efficiency can be achieved by a second EDS detector 24 arranged opposite of the first EDS detector 24. Since the post-field in the SDI mode is still strong enough to bend the total scattered electron beam towards the optical axis 3, the EDS detector 24 is also useable in the SDI mode.

In some embodiments, the EDS detector 24 is mounted on a retractable arm which is configured to move in a linear direction. Such an arrangement allows for retraction of the EDS detector 24 from the pole piece gap area which a lows to operate the STEM in low magnification mode for navigation purposes, where the electromagnetic objective lens 9 is switched off and scattered electrons are not bent to the optical axis 3 so they can directly hit the EDS detector 24. Furthermore, instead of an EDS detector 24 other detectors such as a cathode-luminescence detector or an ultra-High Angle Annular Dark Field (u-HAADF) detector 25 (see below) can be alternatively arranged underneath the sample.

In another embodiment, the retractable EDS detector 24 is linked to the control unit. The electrostatic beam blanker 23 placed between the condenser lens system and the objective electromagnetic lens 9 is also linked to the control unit. If the EDS detector 24 is overexposed, i.e. the electrical signal reaches the safety threshold, the beam blanker 23 blanks the primary beam 2 until the EDS detector 24 processes the incoming signal. After signal processing, the EDS detector 24 reaches again the operation state which causes un-blanking of the primary beam 2 and the measurement can continue.

Figure 7:
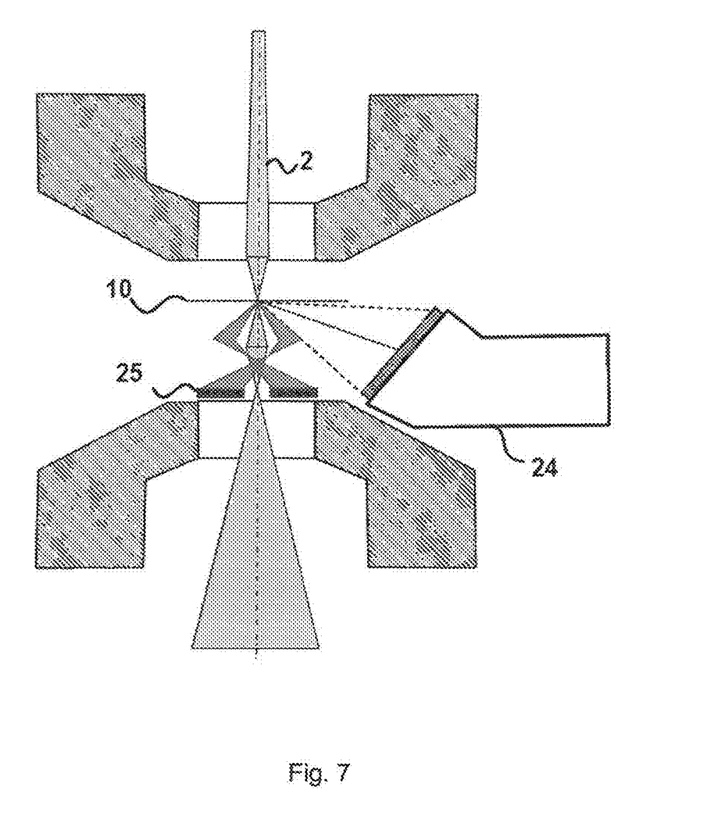
FIG. 7 is a schematic drawing of the arrangement of EDS detector together with u-HAADF detector inside the objective electromagnetic lens.

In yet another embodiment, an ultra-High Angle Annular Dark Field (u-HAADF) detector 25 can be used in addition to the EDS detector 24. The flat u-HAADF detector 25 is arranged close to the lower pole piece face 27 under the first cross-over image. Due to the spherical aberration of the object lens 9a highly scattered electrons (320-720 mrad) are focused far inside the pole piece gap and thus can be detected only by the u-HAADF detector 25. In said embodiment the flat u-HAADF detector 25 does not cause any limitation of the sample tilt compared to arrangement described in U.S. Pat. No. 7,105,816.

Figure 2:
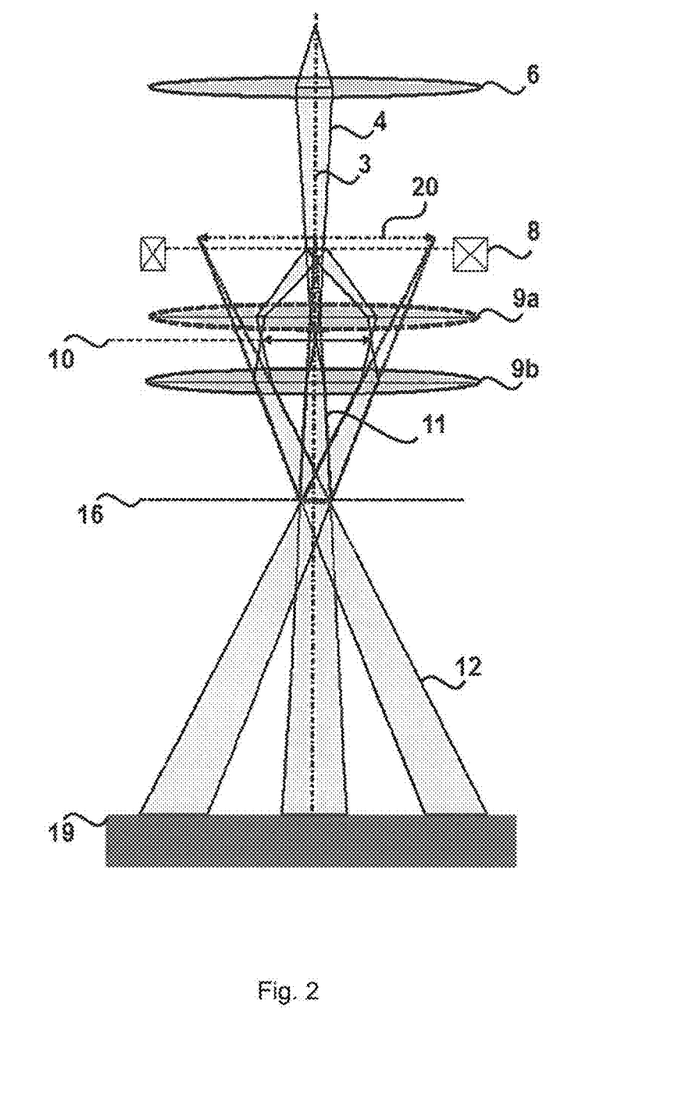
FIG. 2 is schematic drawing of the objective electromagnetic lens in SDI mode.

FIG. 2 is a schematic drawing of the single diffraction mage (SDI) mode of the presented scanning transmission electron microscope. The primary beam 2 is focused onto the sample plane 10 by combination of third condenser lens C3 6 and pre-field lens 9a. Electrons of the primary beam 2 are scattered during the motion through the sample. The excitation of the object lens 9b is chosen in such a way that the first diffraction pattern is formed in the first diffraction plane 16 which is substantially close to the second diffraction plane 18 in the DDI mode. Again, the axial rays 11 form one virtual image 13 in the virtual image plane 20 which is located above the upper pole piece outside the pole piece gap.

In the preferred embodiments, the one diffraction pattern in the SDI mode as well as the second diffraction plane 18 in the DDI are in the vicinity of the lower pole piece face 27 outside the pole piece gap. The distance of said diffraction patterns from the lower pole piece face 27 is (0-1) mm below the lower pole piece face 27 in the direction of the primary beam 2.

Figure 3:
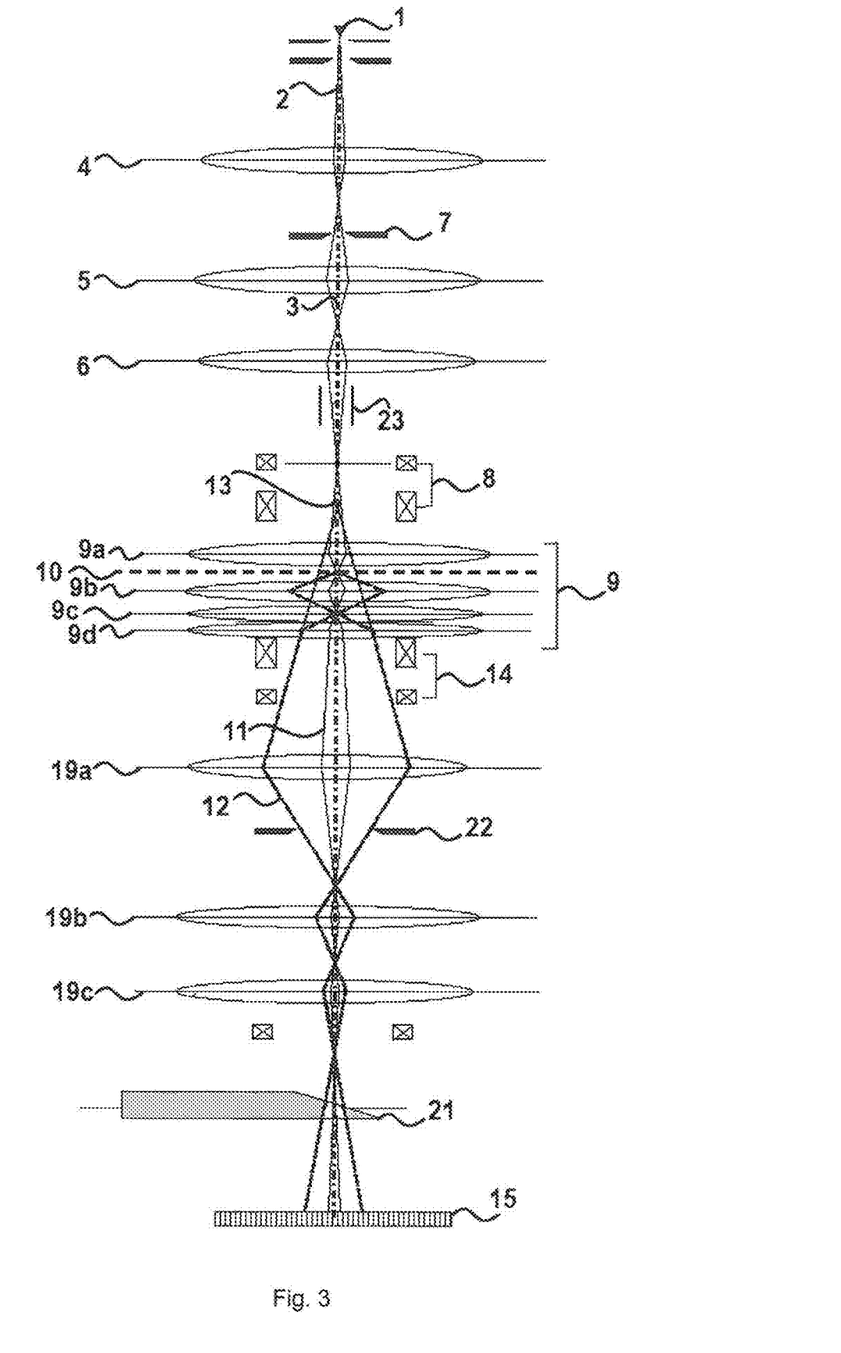
FIG. 3 is a schematic drawing of the objective electromagnetic lens and the projection system.

FIG. 3 is a schematic drawing of an optical set-up and an axial ray 11 path of the presented scanning electron microscope which generally has cylindrical symmetry with respect to the optical axis 3. The primary beam 2 is generated by the electron beam source 1. The primary beam 2 then passes through condenser lens system which consists of a first condenser lens 4, condenser aperture 7, a second condenser lens 5 and a third condenser lens 6. The condenser lens system is configured to change at least one parameter selected from the group of a beam current, a size of the cross-over and a convergence angle. The primary beam 2 is then scanned over the sample by the scanning coils 8. After passing through the sample the axial rays 11 and the field rays 12 are affected by the post-field lenses of the objective electromagnetic lens 9 and they are directed to the projection system 19. For deflecting the beam back to the optical axis the de-scanning/de-precession coils 14 are necessary. The projection system 19 consists of a first projection lens 19a, a second projection lens 19b and a third projection lens 19c. The projection system 19 projects the bright field and/or dark field respectively the diffraction pattern into detection system 15. If only one detector is available, the projection system 19 can be adjusted to transfer either the bright field or the dark field image onto the HAADF detector 21.

From the electron-optical point of view it is useful to operate the first projection lens 19a close to magnification factor of 1. Due to mechanical standpoint, this requires a large distance between the first and the second projection lens. The free space between these two lenses can be used to arrange an intermediate chamber in between. Subsequently, the projection lens system 19 is split into two stages between which this intermediate chamber is placed. The first stage consists of the first projection lens 19a. The second stage consists of the second projection lens 19b and the third projection lens 19c. The intermediate chamber is a separate vacuum housing with a pumping port. It can be used for the arrangement of a gate valve to separate the vacuum system of the objective area from the lower part of the column, mainly the detection area. The intermediate chamber can be also used for a pumping port to keep a low vacuum pressure below the objective electromagnetic lens 9 or for the arrangement of an additional STEM detector to detect a range of DF electrons or the arrangement of a fast post-sample beam blanker for short exposure time and a scattering angle limiting aperture 22 to avoid stray electrons and to get a sharp cut-off of the field of the view of the diffraction pattern.

In yet another embodiment, the second stage can consist of more than two projection lenses.

Figure 4:
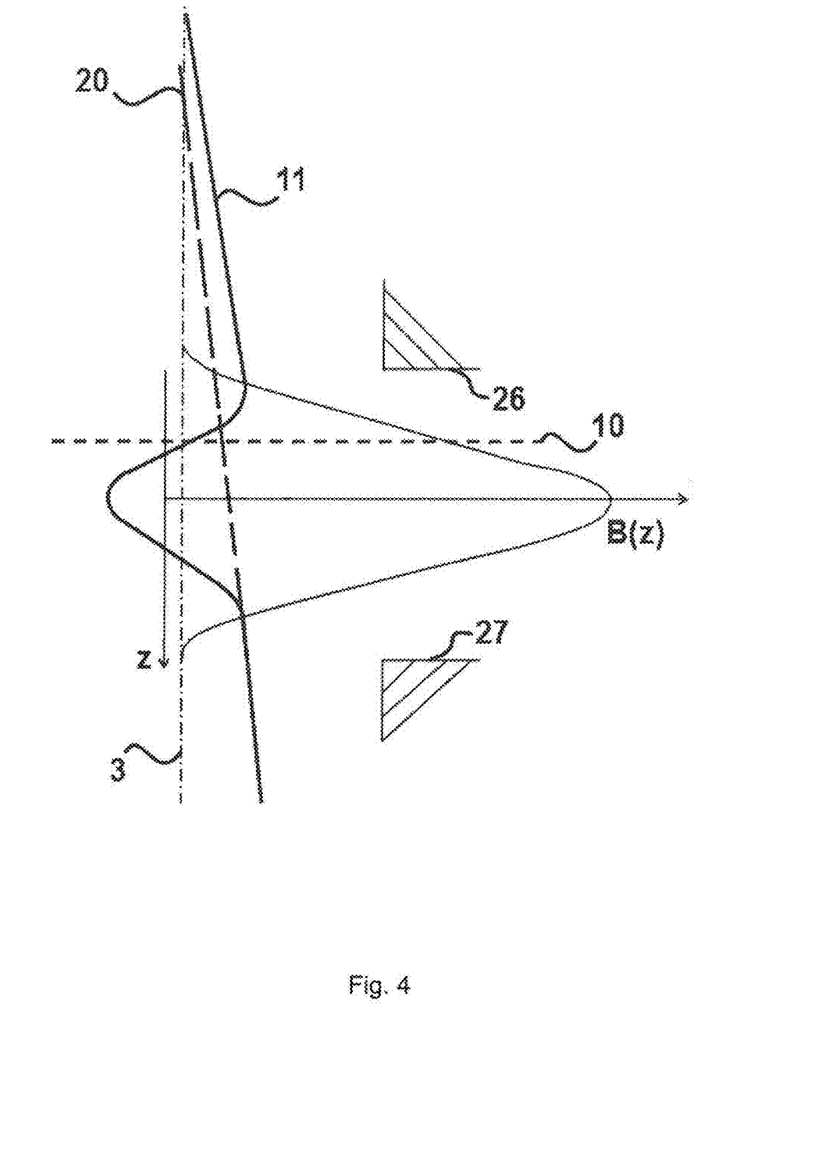
FIG. 4 shows the course of the magnetic field and an axial ray emerging of the cross-over image of the condenser lens system.

FIG. 4 shows the course of the magnetic field inside the pole piece gap, which is a space between an upper pole piece face 26 and a lower pole piece face 27, and an axial ray 11 emerging of the cross-over image (not shown) of the condenser lens system. The axial magnetic field B(z) shaped by the upper and lower pole piece depends on the z coordinate, i.e. the coordinate which corresponds to the optical axis 3. The magnetic field has a cylindrical symmetry. The axial ray 11 entering the magnetic field is bent by the pre-field towards the optical axis 3 in a way that it crosses the optical axis 3 in the sample plane 10 and forms a fine electron probe (cross-over image) in the sample plane 10. In the further course the axial ray 11 is focused by the object lens 9b in the image plane 17. Since the electrons are still in the magnetic field of the objective electromagnetic lens 9 they are (slightly) bent back to the optical axis 3, resulting in a (final) virtual image plane 20 above the upper pole piece (back projection of emerging axial ray=dotted line).

FIG. 5 is a schematic drawing of an arrangement of the Energy Dispersive X-ray (EDS) detector 24 inside the pole piece gap. The primary beam 2 enters the sample plane 10. The interaction of the electrons of the primary beam 2 with the atoms of the sample causes an emission of X-rays. X-ray radiation is detected by the EDS detector 24. The EDS detector 24 is placed under the sample plane 10.

FIG. 6 is a schematic drawing of an arrangement of two EDS detectors 24 inside the pole piece gap. The EDS detectors are arranged opposite to each other. Such an arrangement results in twice the detection efficiency of the single-detector configuration.

FIG. 7 is a schematic drawing of a combination of a u-HAADF detector 25 and an EDS detector 24 inside the pole piece gap. The pole piece gap is a space between the upper pole piece face 26 and the lower pole piece face 27. The primary beam 2 enters the sample plane 10. The interaction of the electrons of the primary beam 2 with the atoms of the sample causes a scattering of the electrons. Part of the electrons is scattered in more less forward direction and can be transferred by the projector lens system to the detection system 15. However, electrons scattered in high angles (>300 mrad) due to spherical aberration generate cross-overs deep inside the pole piece gap so they would hit material before they reach the detector and the information which they provide would be lost. For that reason, the u-HAADF detector 25 is placed just slightly above the lower pole piece face 27 and such electrons are detected by it. Consequently, during the interaction of the electrons of the primary beam 2 with the atoms of the sample the X-rays are emitted. X-ray radiation is then detected by the EDS detector 24 which is placed between the sample plane 10 and the u-HAADF detector 25.

LIST OF MARKS

1—electron source
2—primary beam
3—optical axis
4—first condenser lens C1
5—second condenser lens C2
6—third condenser lens C3
7—condenser aperture
8—scanning/precession coils
9—objective electromagnetic lens
9a—pre-field lens
9b—object lens
9c—first diffraction lens
9d—second diffraction lens
10—sample plane
11—axial rays
12—field rays
13—virtual image
14—de-scanning/de-precession coils
15—detection system
16—first diffraction plane
17—image plane
18—second diffraction plane
19—projection lens system
19a—first projection lens
19b—second projection lens
19c—third projection lens
20—virtual image plane
21—HAADF detector
22—aperture
23—beam blanker
24—EDS detector
25—u-HAADF detector
26—upper pole piece face
27—lower pole piece face

The invention claimed is:

1. A scanning transmission electron microscope comprising an electron source configured to provide a primary electron beam with cross-over, a condenser system, an objective electromagnetic lens comprising an upper pole piece and a lower pole piece forming a pole piece gap configured to provide a pre-field and a post-field with respect to a sample plane located inside the pole piece gap, wherein the upper pole piece comprises an upper pole piece face and the lower pole piece comprises a lower pole piece face, the scanning transmission electron microscope further comprising a projection lens system comprising at least a first projection lens and a second projection lens, and a detection system, wherein at least one diffraction pattern is located in a distance from the lower pole piece face outside the pole piece gap, wherein the distance between the lower pole piece face and the at least one diffraction pattern is in the interval (0-1) mm.

2. The scanning transmission electron microscope according to claim 1 wherein a virtual image plane of the objective electromagnetic lens is located at least 15 mm above a center of the pole piece gap.

3. The scanning transmission electron microscope according to claim 1 wherein the post-field provided by the objective electromagnetic lens is comprised of a triple lens, wherein the triple lens is formed below the sample plane, wherein a first lens of the triple lens is configured to generate a cross-over image in a cross-over image plane and a first diffraction pattern in a first diffraction plane, wherein the cross-over image plane is formed in a vicinity of a principal plane of a second lens of the triple lens, wherein the first diffraction plane is located between the first and the second lens of the triple lens, wherein the first diffraction pattern is projected by the second lens of the triple lens into a second diffraction plane, located in a vicinity of the principal plane of a third lens of the triple lens, wherein the second diffraction pattern is transferred with variable magnification by the projection lens system into the detection system.

4. The scanning transmission electron microscope according to claim 3 wherein an ultra high angle annular dark field detector is placed between the cross-over image plane generated by the first lens of the triple lens and the lower pole piece face.

5. The scanning transmission electron microscope according to claim 1 wherein the sample plane is placed asymmetrically between the upper pole piece face and the lower pole piece face.

6. The scanning transmission electron microscope according to claim 5 wherein a distance between the sample plane and the upper pole piece face is smaller than a distance between the sample plane and the lower pole piece face.

7. The scanning transmission electron microscope according to claim 1 further comprising at least one EDS detector placed between the sample plane and the lower pole piece face.

8. The scanning transmission electron microscope according to claim 7 wherein at least one EDS detector is mounted on an arm, wherein the arm is configured to provide a linear movement of the at least one EDS detector.

9. The scanning transmission electron microscope according to claim 7 further comprising a beam blanker connected to a control unit, wherein the at least one EDS detector is connected to the control unit, wherein the at least one EDS detector is configured to collect an X-ray signal raised by interaction of the primary electron beam with a sample, wherein the at least one EDS detector is configured to transform the X-ray signal to an electrical signal, wherein the control unit is configured to blank the primary electron beam in if the electrical signal provided by the at least one EDS detector reaches the safety threshold value.

10. The scanning transmission electron microscope according to claim 1 further comprising at least two EDS detectors, wherein the at least two EDS detectors are arranged opposite to each other.

11. The scanning transmission electron microscope according to claim 1 wherein an intermediate chamber is placed between the first projection lens and the second projection lens.

12. A method of providing double diffraction pattern, bright field image and dark field image in a scanning transmission electron microscope comprising an electron source configured to provide a primary electron beam with cross-over, a condenser system, an objective electromagnetic lens comprising an upper pole piece and a lower pole piece configured to provide a pre-field and a post-field, wherein the upper pole piece comprises an upper pole piece face and the lower pole piece comprises a lower pole piece face, a sample plane, a projection lens system and a detection system, the method comprises the steps of:
   a) passing electrons by the sample plane to generate at least one diffraction pattern,
   b) locating the at least one diffraction pattern in distance from the lower pole piece face outside a pole piece gap, wherein the distance between the lower pole piece face and the at least one diffraction pattern is in the interval (0-1) mm, and
   c) generating a virtual cross-over image in a virtual image plane, wherein the virtual image plane is located at least 15 mm above a center of the pole piece gap.

13. The method according to claim 12 wherein the post-field provided by the objective electromagnetic lens is comprised of a triple lens, wherein the triple lens is formed below the sample plane, wherein a first lens of the triple lens generates a cross-over image in a cross-over image plane and a first diffraction pattern in a first diffraction plane, wherein the cross-over image plane is in a second lens of the triple lens, wherein the diffraction plane is between the first and the second lens of the triple lens, wherein the first diffraction pattern is projected by the second lens of the triple lens into a second diffraction plane, wherein the second diffraction plane is located close to a principal plane of a third lens of the triple lens, wherein the second diffraction pattern is transferred by the projection lens system with variable magnification into the detection system.

14. The method according to claim 12 wherein a third condenser lens C3 generates a focused cross-over image in the sample plane.

15. A method of providing single diffraction pattern, bright field image and dark field image in a scanning transmission electron microscope comprising an electron source configured to provide a primary beam with cross-over, a condenser system, an objective electromagnetic lens comprising an upper pole piece and a lower pole piece configured to provide a pre-field and a post-field with respect to a sample plane located inside a pole piece gap, wherein the upper pole piece comprises an upper pole piece face and the lower pole piece comprises a lower pole piece face, a projection lens system and a detection system, wherein the post-field provided by the objective electromagnetic lens is comprised of a single lens, the method comprises the steps of:
   a) forming the single lens between the sample plane and the lower pole piece face,
   b) generating, by the single lens, a virtual cross-over image in a virtual image plane and a single diffraction pattern,
   c) locating the diffraction pattern in a distance from the lower pole piece face outside the pole piece gap, wherein the distance between the lower pole piece face and diffraction pattern is in the interval (0-1) mm, and
   d) transferring the diffraction pattern with variable magnification by the projection lens system into the detection system.

16. The method according to claim 15 wherein a third condenser lens C3 generates a focused cross-over image in the sample plane.

* * * * *